United States Patent
Hannay

(10) Patent No.: US 9,517,147 B2
(45) Date of Patent: Dec. 13, 2016

(54) HELICAL ARM TIE DOWN

(71) Applicant: Cook Medical Technologies LLC, Bloomington, IN (US)

(72) Inventor: Gwynne Hannay, Queensland (AU)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 14/713,264

(22) Filed: May 15, 2015

(65) Prior Publication Data
US 2015/0245929 A1    Sep. 3, 2015

Related U.S. Application Data

(63) Continuation of application No. 12/075,531, filed on Mar. 12, 2008, now Pat. No. 9,034,030.
(Continued)

(51) Int. Cl.
*A61F 2/06*        (2013.01)
*A61F 2/856*      (2013.01)
(Continued)

(52) U.S. Cl.
CPC ............... *A61F 2/856* (2013.01); *A61F 2/07* (2013.01); *A61F 2/844* (2013.01); *A61F 2/89* (2013.01);

Related U.S. Application Data

(60) Provisional application No. 60/906,477, filed on Mar. 12, 2007.

(58) Field of Classification Search
CPC ...................................................... A61F 2/856
See application file for complete search history.

(56) References Cited

U.S. PATENT DOCUMENTS 6,471,722 B1    10/2002    Inoue
7,105,020 B2     9/2006    Greenberg et al.
(Continued)

FOREIGN PATENT DOCUMENTS

CA    2518890         10/2004
CA    2518890 A1      10/2004
(Continued)

OTHER PUBLICATIONS

International Search Report for corresponding PCT/US2008/003319 dated Jul. 7, 2008, 5 pages.
(Continued)

*Primary Examiner* — Jacqueline Woznicki
(74) *Attorney, Agent, or Firm* — Brinks Gilson & Lione

(57) ABSTRACT

A stent graft having a tubular body with a ostium in the side wall of the tubular body and a side arm extending from the ostium. The side arm comprising a tube of graft material extending at least partially helically around and longitudinally along the tubular body of the stent graft at least one-fourth the circumference of the tubular body to an open end and has a resilient reinforcing ring attached about and encircling its open end. The resilient reinforcing ring is permanently attached to the tubular body with a tie down arrangement that passes through the graft material of the tubular body and through the side arm and engages the resilient reinforcing ring to permanently hold the open end of the side arm against the tubular body surface. A line of radiopaque markers extends along the length of the side arm from the ostium to the open end.

10 Claims, 1 Drawing Sheet

(51) Int. Cl.
*A61F 2/07* (2013.01)
*A61F 2/844* (2013.01)
*A61F 2/95* (2013.01)
*A61F 2/954* (2013.01)
*A61F 2/82* (2013.01)
*A61F 2/89* (2013.01)

(52) U.S. Cl.
CPC .................. *A61F 2/95* (2013.01); *A61F 2/954* (2013.01); *A61F 2002/061* (2013.01); *A61F 2002/065* (2013.01); *A61F 2002/821* (2013.01); *A61F 2220/0025* (2013.01); *A61F 2220/0075* (2013.01); *A61F 2230/0069* (2013.01); *A61F 2250/0098* (2013.01)

(56) References Cited

U.S. PATENT DOCUMENTS

| | | |
|---|---|---|
| 2003/0120333 A1 | 6/2003 | Ouriel et al. |
| 2004/0243221 A1 | 12/2004 | Fawzi et al. |
| 2006/0247761 A1* | 11/2006 | Greenberg ................ A61F 2/07 623/1.16 |

FOREIGN PATENT DOCUMENTS

| | | |
|---|---|---|
| WO | WO 98/19630 | 5/1998 |
| WO | WO 98/19630 A2 | 5/1998 |
| WO | WO 99/22671 | 5/1999 |
| WO | WO 99/22671 A2 | 5/1999 |
| WO | WO 2004/089249 A1 | 10/2004 |
| WO | WO 2006/113501 A1 | 10/2006 |
| WO | WO 2007/025101 A2 | 3/2007 |
| WO | WO 2008/112270 A1 | 9/2008 |

OTHER PUBLICATIONS

International Written Opinion for corresponding PCT/US2008/003319 dated Jul. 7, 2008, 8 pages.
International Preliminary Report on Patentability for corresponding PCT/US2008/003319 dated Sep. 24, 2009, 9 pages.
International Search Report for corresponding application No. PCT/US2008/003319, dated Jul. 7, 2008, 3 pgs.
International Preliminary Search Report for corresponding application No. PCT/US2008/003319, dated Sep. 15, 2009, 8 pgs.

* cited by examiner

HELICAL ARM TIE DOWN

RELATED APPLICATIONS

The patent application is a continuation of application Ser. No. 12/075,531, filed Mar. 12, 2008, which claims the benefit of the filing date under 35 U.S.C. §119(e) of Provisional U.S. Patent Application Ser. No. 60/906,477, filed Mar. 12, 2007. All of the foregoing applications are hereby incorporated by reference.

TECHNICAL FIELD

This invention relates to a medical device and more particularly to an arrangement for assembly of a medical device onto an introduction device.

BACKGROUND OF THE INVENTION

This invention will be particularly discussed in relation to stent grafts for placement into the thoracoabdominal aorta for the treatment of aneurysms and more specifically in relation to juxtarenal placement. The invention, however, is not so restricted and may be applied to stent grafts for placement in any lumen of the human or animal body.

There has been devised a thoracoabdominal stent-graft with one or more side arms for the celiac, superior mesenteric and/or renal arteries. One particular form of stent graft includes a side arm which is a graft material tube which extends at least partially helically around the stent graft from a fenestration or ostium in the stent graft. Such a graft material tube can be formed from a corrugated graft material.

U.S. Pat. No. 7,105,020 entitled "Branched Vessel Endoluminal Device" describes various forms of helically extending side arm stent grafts and the teaching therein is incorporated herein in its entirety.

These helically extending side arm stent grafts may include radiopaque markers along the length of the helical branch to assist a physician with correct placement by radiographic techniques of the helically extending side arm stent graft into the aorta of a patient with the open end of the side arm directed towards a branch vessel of the aorta. The stent graft is constricted into an introduction device under a delivery sheath for introduction into a patient using endovascular techniques and during assembly onto the introduction device the side arm can be distorted out of its helical position. This can make the correct radiographic visualization of the position of the open end very difficult during the introduction procedure.

It is the object of this invention to provide an arrangement by which the side arm is constrained during assembly so that it remains in a desired position for introduction.

Although the invention will be generally discussed in relation to side arms for stent grafts which extend helically around a stent graft body the invention is not so restricted and may also be applied to other forms of side arm.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

BRIEF SUMMARY

In one form the invention is said to reside in a stent graft comprising a tubular body of a biocompatible graft material and a side arm extending therefrom, the side arm extending from an ostium in the tubular body and at least partially along the tubular body to an open end of the side arm and a temporary tie down arrangement for the side arm at least adjacent to the open end, whereby to hold flat the open end of the side arm during loading of the stent graft into a deployment device to ensure the side arm is retained in its position with respect to the tubular body.

Preferably the temporary tie down arrangement comprises a tie down wire stitched into the graft material adjacent to the side arm and through the side arm to hold the side arm against the tubular body.

Preferably the side arm comprises a plurality of radiopaque markers therealong.

Preferably the side arm comprises a transversely corrugated graft material tube and the open end of the side arm extends at an angle of approximately 45° to the longitudinal direction of the stent graft.

Preferably the side arm comprises a resilient reinforcing ring at the open end thereof. The resilient reinforcing ring at the open end of the side arm can be permanently stitched to the tubular body. By this arrangement the resilient reinforcing ring at the open end of the side arm is held flat, with the open end against the tubular body, by the temporary tie down arrangement.

There can be further included a second temporary tie down arrangement for the side arm adjacent to hold flat the ostium end of the side arm during loading of the stent graft into a deployment device.

In one embodiment the temporary tie down arrangement is removed after the stent graft is loaded into a deployment device. Alternatively the temporary tie down arrangement is retained after the stent graft is loaded into a deployment device and the deployment device includes a release arrangement for the temporary tie down arrangement.

In one embodiment the side arm is a helical side arm which extends substantially helically around and along the tubular body of the stent graft.

In an alternative form the invention comprises a stent graft comprising a tubular body of a biocompatible graft material and a side arm extending therefrom, the side arm comprising a transversely corrugated graft material tube and a plurality of radiopaque markers therealong, the side arm extending from an ostium in the tubular body and substantially helically around and along the tubular body to an open end and the side arm comprising a resilient reinforcing ring permanently stitched to the tubular body at the open end thereof, a first temporary tie down arrangement comprising a tie down wire stitched into the graft material adjacent to the side arm and through the side arm to hold the side arm against the tubular body adjacent to the open end, and a second temporary tie down arrangement for the side arm at the ostium end thereof whereby to hold flat the open end of the side arm and the ostium end of the side arm during loading of the stent graft into a deployment device to ensure the side arm retains its position with respect to the tubular body.

In an alternative form the invention comprises a method of temporarily retaining a side arm of a stent graft in a selected position during loading thereof onto a deployment device, the stent graft comprising a tubular body of a biocompatible graft material and the side arm extending therefrom, the side arm comprising a plurality of radiopaque markers therealong, the side arm extending from an ostium in the tubular body and substantially helically around and along the tubular body to an open end;

The method including the steps of;
(a) stitching a first tie down wire through the biocompatible graft material of the tubular body and through the side arm and then through the biocompatible graft material of the tubular body at the open end of the side arm;
(b) stitching a second tie down wire through the biocompatible graft material of the tubular body and through the side arm and then through the biocompatible graft material of the tubular body at the ostium end of the side arm;
(c) loading the stent graft into a sheath of a deployment device for the stent graft; and
(d) optionally removing the first and/or second tie down wires after the stent graft is loaded into the sheath.

BRIEF DESCRIPTION OF THE DRAWINGS

This then generally describes the invention but to assist with understanding reference will now be made to preferred embodiments with the assistance of the accompanying drawings in which.

DETAILED DESCRIPTION OF THE DRAWINGS

Figure 1:
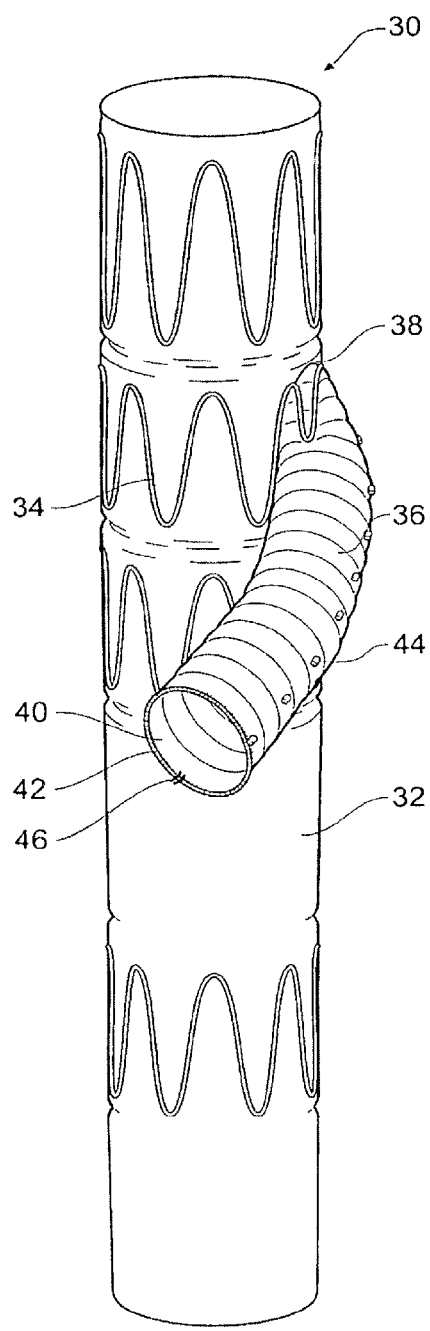
FIG. 1 shows a stent graft including a side arm according to one embodiment of the invention.
Figure 2:
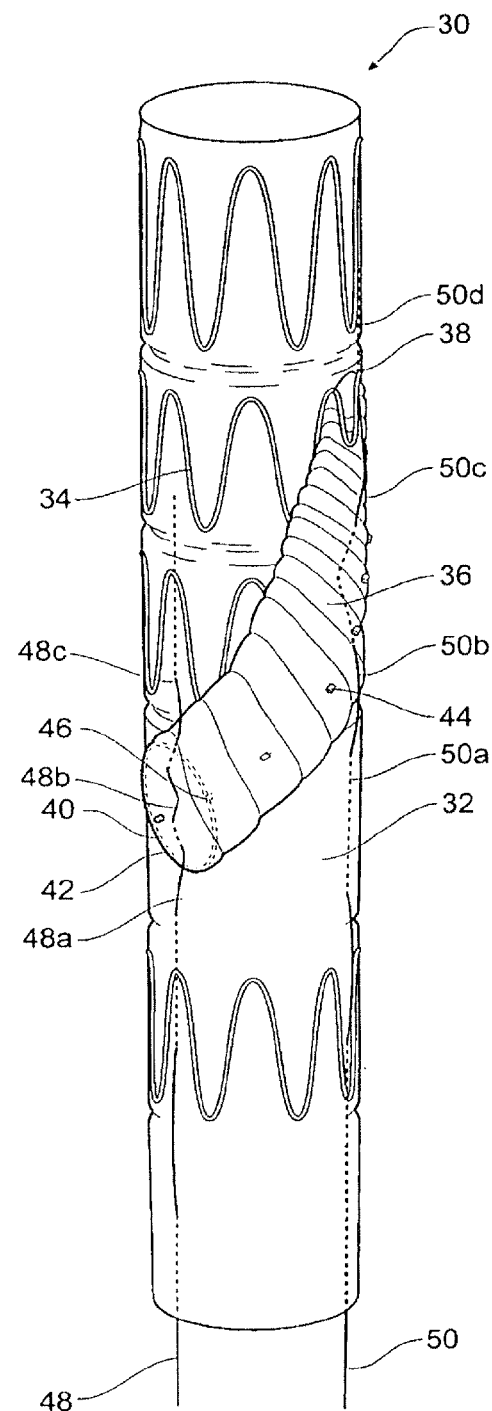
FIG. 2 shows the embodiment of FIG. 1 with two temporary tie down arrangements applied to it.

Looking at FIGS. 1 and 2 there is shown an embodiment of the invention.

In FIGS. 1 and 2 a stent graft 30 is formed from a tubular body 32 of a biocompatible graft material and has a plurality of zig-zag self expanding stents 34. A tubular side arm 36 extends from an ostium or fenestration 38 in the tubular body 32 in a part helical configuration along and around the tubular body 32 to an open end 40. The open end 20 is directed at an angle of approximately 45° to the longitudinal direction of the tubular body 32 and is reinforced by a resilient ring 42 stitched to the open end 40. The side arm 36 has a line of radiopaque markers 44 along its length. The tubular side arm 36 is formed from a corrugated biocompatible graft material tube and does not have any stents along its length. The resilient ring 42 is stitched to the tubular body 32 by stitching 46 to hold the open end in a desired position.

If the stent graft 30 was to be constricted and be forced into a sheath of a deployment device at least part of the side arm and the open end 40 of the side arm 36 could be dragged into line with the length of the tubular body 32 which removes the helical form of the line of radiopaque markers 44 and makes it more difficult to visualize the position of the open end and place it in a desired position with respect to a side branch of a body vessel.

FIG. 2 shows the side arm 36 tied down by the use of a pair of tie down wires 48 and 50. A first tie down wire 48 is stitched through the graft material of the tubular body 32 at 48a, through the graft material of the side arm adjacent to the open end 40 at 48b and then through the graft material of the tubular body 32 on the other side of the side arm 36 at 48c. The tie down wire 48 holds the resilient ring 42, hinged about the stitching 46 with the open end 40 against the tubular body 32.

A second tie down wire 50 is stitched through the graft material of the tubular body 32 at 50a, through the graft material of the side arm towards the ostium end of the side arm at 50b, out of the side arm again at 50c and then through the graft material of the tubular body 32 on the other side of the ostium 38 of the side arm 36 at 50d.

By this arrangement the side arm is held in its desired position during constriction and loading onto a delivery sheath. This will assist in retaining the relative position of the helical line of radiopaque markers 24 with respect to the tubular body. As these can be visualized through the delivery sheath during an endovascular delivery operation the position of the open end 40 of the side arm can be determined and it will not significantly change when the delivery sheath is withdrawn.

After the stent graft has been placed into the delivery sheath in its constricted form (not shown) the tie down wires 48 and 50 can be withdrawn. Alternatively the tie down wires can be left in place and a suitable release mechanism provided on the delivery device to enable release at a selected time during the delivery procedure. It may be desirable to be able to rotate or move longitudinally the stent graft on the delivery device after withdrawal of the delivery sheath and before the side arm is released. This could prevent the side arm from fouling with the wall of the vessel during rotational and longitudinal movement.

Throughout this specification various indications have been given as to the scope of the invention but the invention is not limited to any one of these but may reside in two or more of these combined together. The examples are given only for illustration and not for limitation.

The invention claimed is:

1. A stent graft comprising a tubular body of a biocompatible graft material having a side wall and an ostium in the side wall of the tubular body,
   the tubular body having a circumference, a proximal end, a distal end, a tubular body surface, and a side arm extending from the ostium between the proximal end and the distal end, the side arm comprising a tube of graft material extending at least partially helically around and longitudinally along the tubular body of the stent graft at least one-fourth the circumference of the tubular body to an open end,
   the side arm comprising a resilient reinforcing ring attached about and encircling its open end, where the resilient reinforcing ring is permanently attached to the tubular body with a tie down arrangement that passes through the graft material of the tubular body and through the side arm and engages the resilient reinforcing ring to permanently hold the open end of the side arm against the tubular body surface,
   a temporary tie down arrangement for the side arm, separate from the first tie down arrangement, the temporary tie down arrangement comprising at least one elongate longitudinally extending wire extending proximally of the ostium end of the side arm to distally of the ostium of the side arm and holding flat the ostium end of the side arm during loading of the stent graft into a deployment device,
   wherein the side arm has a length extending from the ostium to its open end and comprises a line of radiopaque markers extending along substantially the length of the side arm from the ostium to the open end, and wherein the line of radiopaque markers comprises a helical line relative to the tubular body of the stent graft.

2. The stent graft of claim 1, wherein the side arm extends at an angle of approximately 45° to the longitudinal direction of the stent graft.

3. The stent graft of claim 2, wherein the side arm is unstented.

4. The stent graft of claim 1, wherein the side arm comprises a transversely corrugated graft material tube.

5. The stent graft of claim 1, further comprising at least two discrete spaced apart stent rings attached to an outer surface of the tubular body.

6. The stent graft of claim 5, wherein one of the at least two discrete spaced apart stent rings encircles the circumference of the tubular body and the ostium end of the side arm.

7. A stent graft comprising a tubular body of a biocompatible graft material having a proximal end, a distal end, a side wall and an ostium in the side wall of the tubular body between the proximal end and the distal end, the tubular body having a circumference, a tubular body surface, and a side arm extending from the ostium, the side arm comprising a transversely corrugated, unstented tube of graft material extending at least partially helically around and along the tubular body of the stent graft at least one-fourth the circumference of the tubular body to an open end, the side arm comprising a resilient reinforcing ring attached about and encircling its open end, where the resilient reinforcing ring is permanently attached to the tubular body with a tie down arrangement that passes through the graft material of the tubular body and through the side arm and engages the resilient reinforcing ring to permanently hold the open end of the side arm against the tubular body surface, wherein the side arm has a length extending from the ostium to its open end and comprises a line of radiopaque markers extending along substantially the length of the side arm from the ostium to the open end, and wherein the line of radiopaque markers comprises a helical line relative to the tubular body of the stent graft, and a temporary tie down arrangement for the side arm, separate from the first tie down arrangement, the temporary tie down arrangement comprising at least one elongate longitudinally extending wire extending proximally of the ostium end of the side arm to distally of the ostium of the side arm and holding flat the ostium end of the side arm during loading of the stent graft into a deployment device.

8. The stent graft of claim 7, wherein the side arm extends at an angle of approximately 45° to the longitudinal direction of the stent graft.

9. The stent graft of claim 7, further comprising at least two discrete spaced apart stent rings attached to an outer surface of the tubular body.

10. The stent graft of claim 9, wherein one of the least two discrete spaced apart stent rings encircles the circumference of the tubular body and the ostium end of the side arm.

* * * * *